United States Patent [19]

Stables

[11] Patent Number: 5,466,436
[45] Date of Patent: Nov. 14, 1995

[54] MEDICAMENTS FOR TREATING INFLAMMATORY CONDITIONS OR FOR ANALGESIA

[75] Inventor: Roger Stables, Ware, Great Britain

[73] Assignee: Glaxo Group Limited, London, England

[21] Appl. No.: 168,231

[22] Filed: Dec. 17, 1993

Related U.S. Application Data

[63] Continuation of Ser. No. 986,019, Dec. 4, 1992, abandoned.

[30] Foreign Application Priority Data

Dec. 6, 1991 [GB] United Kingdom .................. 9126027
Mar. 20, 1992 [GB] United Kingdom .................. 9206083

[51] Int. Cl.$^6$ .......................... A61K 49/00; A61K 31/62; A61K 31/555
[52] U.S. Cl. ........................ 514/161; 514/184; 514/925
[58] Field of Search ............... 424/10; 514/184, 514/159, 922, 161, 925

[56] References Cited

U.S. PATENT DOCUMENTS

| | | | |
|---|---|---|---|
| 4,855,293 | 8/1989 | Collington et al. | 514/212 |
| 5,008,256 | 4/1991 | Clitherow | 514/184 |
| 5,128,140 | 7/1992 | Chapura et al. | 424/451 |

FOREIGN PATENT DOCUMENTS

| | | |
|---|---|---|
| 0282132 | 9/1988 | European Pat. Off. . |
| 2105193 | 3/1983 | United Kingdom . |
| 2248185 | 4/1992 | United Kingdom . |

OTHER PUBLICATIONS

Hudson et al. Gut 1992, Supplement 33:S47.
Baxter et al., Gut 1991, 32, A1227.
Ehsanullah et al., British Medical Journal (1988), 297, 1017–1021.
Robinson et al., Digestive Diseases and Science, 34, No. 3, 424–428 (1989).
Kitchingman et al., British J. Clinical Pharmacology (1989), 28, 581–585.
Konturek et al., Scandinavian J. Gastroenterology (1988), 23, 861–866.
Hardo et al., J. Drug Development (1990), 3(3), 151–153.
Pazzi et al., Argomenti di Gastroenterologia Clinica (1990), 3, 85–91.

*Primary Examiner*—Raymond Henley, III
*Attorney, Agent, or Firm*—Bacon & Thomas

[57] ABSTRACT

The use is described of both (i) ranitidine bismuth citrate and (ii) a non-steroidal anti-inflammatory drug in treating or preventing inflammatory conditions and for analgesia. Pharmaceutical compositions containing both (i) and (ii) and methods for the preparation of pharmaceutical compositions containing (i) and (ii) are also described.

15 Claims, No Drawings

MEDICAMENTS FOR TREATING INFLAMMATORY CONDITIONS OR FOR ANALGESIA

This application is a continuation of application Ser. No. 07/986,019, filed Dec. 4, 1992.

The present invention relates to improvements in the treatment of inflammatory conditions and for analgesia. More particularly it relates to the co-administration of a non-steroidal anti-inflammatory drug with a salt formed between ranitidine and a complex of bismuth with a carboxylic acid.

Systemic non-steroidal anti-inflammatory drugs, such as aspirin, indomethacin, ibuprofen and piroxicam, are known to give rise to undesirable side effects. In particular, they are known to be ulcerogenic and can thus, for example, give rise to gastric and/or duodenal ulceration when administered orally. This side effect may be further enhanced in combination with other factors such as stress and smoking. Since in some treatments these compounds may have to be used for an extended period, such side effects can prove a serious disadvantage.

In our UK Patent Specification No. 2220937B we describe and claim salts formed between ranitidine and a complex of bismuth with a carboxylic acid, particularly tartaric acid and, more especially, citric acid. One such salt is N-[2-[[[5-[(dimethylamino)methyl] -2-furanyl]methyl] thio]ethyl]-N'-methyl-2-nitro-1,1-ethenediamine 2-hydroxy-1,2,3-propanetricarboxylate bismuth ($3^+$) complex, also known as ranitidine bismuth citrate.

The salts disclosed in UK Patent Specification No. 2220937B possess the $H_2$-antagonist antisecretory properties associated with ranitidine, together with antibacterial activity against *Helicobacter pylori* (formerly *Campylobacter pylori*). In addition, such salts possess cytoprotective properties and display activity against the human gastric pepsins with preferential inhibition of pepsin 1, a pepsin isozyme associated with peptic ulcer. The salts disclosed in UK Patent Specification No. 2220937B thus possess a particularly advantageous combination of properties for the treatment of gastrointestinal disorders, especially peptic ulcer disease (e.g. gastric and duodenal ulceration) and other gastroduodenal conditions, for example gastritis and non-ulcer dyspepsia.

Tests in animals and humans have now shown that mucosal lesions of the gastrointestinal tract caused by non-steroidal anti-inflammatory drugs are significantly reduced by administering ranitidine bismuth citrate. In particular, we have demonstrated in rats the ability of ranitidine bismuth citrate to prevent indomethacin induced gastric antral ulceration using a modification of the method of Satoh et al., Gastroenterology (1981), 81, 719–725. In this test ranitidine bismuth citrate was markedly more potent than both ranitidine hydrochloride and tripotassium dicitrato bismuthate as DeNol™. A recently published human clinical study (N. Hudson et al., Gut 1992, 33 supplement, s47) also demonstrates that ranitidine bismuth citrate confers substantial protection from aspirin-induced injury to the gastric mucosa.

The present invention thus provides, in one aspect, the use of (i) ranitidine bismuth citrate and (ii) a non-steroidal anti-inflammatory drug in the manufacture of medicaments for simultaneous, separate or sequential use in treating or preventing inflammatory conditions or for analgesia.

In a further, or alternative, aspect the present invention provides the use of ranitidine bismuth citrate in the manufacture of medicaments to prevent gastrointestinal damage caused by non-steroidal anti-inflammatory drugs.

Combination therapy according to the present invention may be used in the treatment of inflammatory conditions, particularly acute and chronic musculo-skeletal inflammatory conditions such as rheumatoid and osteo-arthritis and ankylosing spondylitis and for analgesia in conditions such as dysmenorrhoea, especially where the use of the anti-inflammatory drug is limited by gastrointestinal side effects. As stated above, co-administration of ranitidine bismuth citrate with a systematic non-steroidal anti-inflammatory drug may also be used to prevent gastrointestinal damage caused by non-steroidal anti-inflammatory drugs. Such gastrointestinal damage includes duodenal and/or gastric ulceration, non-steroidal anti-inflammatory drug associated gastritis and gastric erosions, and non-steroidal anti-inflammatory drug associated mucosal damage to the small intestine.

Suitable systemic non-steroidal anti-inflammatory drugs which may be employed in the invention generally also show analgesic activity and include, for example, aspirin, indomethacin, ibuprofen, piroxicam, fenoprofen, ketoprofen, naproxen, mefenamic acid, diflunisal, benorylate, azapropazone, diclofenac, fenbufen, feprazone, fenclofenac, fiufenamic acid, flurbiprofen, oxyphenbutazone, phenylbutazone, sulindac and tolmetin.

The ranitidine bismuth titrate and the anti-inflammatory drug are preferably co-administered in the form of separate pharmaceutical compositions for simultaneous and/or sequential use. Alternatively the ranitidine bismuth citrate and the anti-inflammatory drug may be administered as a single pharmaceutical composition for oral use comprising effective amounts of the active ingredients.

Thus, according to a further aspect, the invention provides a product containing (i)ranitidine bismuth citrate and (ii) a non-steroidal anti-inflammatory drug as a combined preparation for simultaneous, separate or sequential use in treating or preventing inflammatory conditions or for analgesia.

When the ranitidine bismuth citrate and the non-steroidal anti-inflammatory are administered as separate preparations, the anti-inflammatory may be provided in any convenient formulation, such as in the manner known in the art and/or commercially for the compound concerned. Administration of both the ranitidine bismuth citrate and the non-steroidal anti-inflammatory by the oral route is preferred, although the anti-inflammatory, where appropriate, may also be given by another route, for example parenterally (e.g. intravenously) or rectally (e.g. by suppository).

The ranitidine bismuth citrate may conveniently be formulated as tablets (including chewable tablets), capsules (of either the hard or soft type), or as a liquid preparation, as described for example in UK Patent Specification Nos. 2220937B and 2248185A. Tablets are generally preferred.

As stated hereinabove, ranitidine bismuth citrate and the non-steroidal anti-inflammatory drug may be administered as a single pharmaceutical composition for oral use. Thus, according to a further aspect the invention provides a pharmaceutical composition, for oral use in human or veterinary medicine, comprising ranitidine bismuth citrate and a non-steroidal anti-inflammatory drug, together, where appropriate, with a pharmaceutically acceptable carrier or excipient.

Suitable additional carriers or excipients include binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate,. talc or silica); disintegrants (e.g. starch or sodium starch glycollate); or wetting agents (e.g. sodium lauryl sulphate). An alkaline salt of the type described in UK Patent Specification No. 2248185A may be added to improve the rate of disintegration and/or dissolution of the composition.

The compositions may be prepared according to conventional techniques well known in the pharmaceutical industry. Thus, for example, the ranitidine bismuth citrate and the non-steroidal anti-inflammatory drug may be admixed together, if desired, with suitable carriers or excipients. Tablets may be prepared, for example, by direct compression or wet granulation of such a mixture. Capsules may be prepared by filling the blend along with suitable carriers or excipients into gelatin capsules, using a suitable filling machine. Tablets may be coated by methods well known in the art. The preparations may also contain flavouring, colouring and/or sweetening agents as appropriate.

When ranitidine bismuth citrate and the non-steroidal anti-inflammatory drug are administered as a single pharmaceutical composition for oral use the composition is preferably in the form of a capsule or, more particularly, a tablet.

The compositions for use according to the invention may, if desired, be presented in a pack or dispenser device which may contain one or more unit dosage forms containing the active ingredients. The pack may for example comprise metal or plastic foil, such as a blister pack. Where the ranitidine bismuth citrate and the non-steroidal anti-inflammatory drug are intended for administration as separate compositions these may be presented in the form of, for example, a twin pack.

Thus, according to a further aspect the present invention provides a twincontainer pack for use in treating or preventing inflammatory conditions or for analgesia, one of the containers containing ranitidine bismuth citrate and the other containing a non-steroidal anti-inflammatory drug.

The doses at which the ranitidine bismuth citrate and the non-steroidal anti-inflammatory may be administered to man (of approximately 70kg body weight) will depend on the route of administration of the anti-inflammatory and on the nature and severity of the condition being treated. It will also be appreciated that it may be necessary to make routine variations to the dosage depending on the age and weight of the patient.

A proposed dosage of ranitidine bismuth citrate for use according to the invention is 150mg to 1.5g, preferably 200–800mg per unit dose. The unit dose may be administered, for example, 1 to 4 times per day, preferably once or twice per day.

The non-steroidal anti-inflammatory may conveniently be administered at doses within the normal dosage range at which the compound is therapeutically effective, for example 50mg–1 g of aspirin, 10–100 mg of indomethacin, 5–50 mg of piroxicam, 100–500mg of ibuprofen and 200–800mg of mefenamic acid per dosage unit taken one or more times daily in accordance with the normal dosage regime for the drug in question.

In a further aspect, the present invention provides a method of treating inflammatory conditions or for analgesia in a human or animal subject, which comprises administering to said subject effective amounts of ranitidine bismuth citrate and a non-steroidal anti-inflammatory drug.

In another, or alternative, aspect the present invention provides a method of treating gastrointestinal damage caused by non-steroidal anti-inflammatory drugs in a human or animal subject, which comprises administering to said subject an effective amount of ranitidine bismuth citrate.

References herein to treatment include prophylactic treatment as well as the alleviation of acute symptoms.

The methods of the present invention comprise administering the non-steroidal anti-inflammatory drug and ranitidine bismuth citrate either concurrently or non-concurrently. As used herein, concurrent administration means that the agents are given within 24 hours of each other, whereas non-concurrent administration means that the agents are given more than 24 hours apart. When the agents are administered concurrently, it may be preferable to administer the agents within about 1 hour of each other or, more preferably, within about 5 minutes of each other.

For the methods of the present invention, the duration of administration of the agents during either concurrent or non-concurrent dosing will vary according to the specific condition being treated.

The following examples illustrate pharmaceutical compositions for oral use containing both ranitidine bismuth citrate and a suitable non-steroidal anti-inflammatory drug.

EXAMPLE 1

TABLETS

|  | mg/tablet |
|---|---|
| (a) Ranitidine bismuth citrate | 400.00 |
| Ibuprofen | 400.00 |
| Lactose | 200.00 |
| Hydroxypropyl methylcellulose | 5.00 |
| Sodium starch glycollate | 30.00 |
| Magnesium stearate | 10.00 |
| Compression weight | 1045.00 |

The ranitidine bismuth citrate and ibuprofen are sieved through a 250μm sieve and blended with the lactose. This mix is granulated with a solution of the hydroxypropyl methylcellulose. The granules are dried, screened and blended with the sodium starch glycollate and the magnesium stearate. The lubricated granules are compressed into tablets using 15.0mm punches.

|  | mg/tablet |
|---|---|
| (b) Ranitidine bismuth citrate | 400.00 |
| Indomethacin | 50.00 |
| Microcrystalline cellulose | 114.00 |
| Anhydrous sodium carbonate | 30.00 |
| Magnesium stearate | 6.00 |
| Compression weight | 600.00 |

The ranitidine bismuth citrate and indomethacin are blended with the microcrystalline cellulose, sodium carbonate and magnesium stearate and compressed using 12.5mm punches.

EXAMPLE 2

CAPSULES

|  | Capsule |
|---|---|
| (a) Ranitidine bismuth citrate | 200.00 |
| Ibuprofen | 400.00 |
| Starch 1500** | 196.00 |

-continued

|  | Capsule |
|---|---|
| Magnesium stearate | 4.00 |
| Fill weight | 800.00 |

**A form of directly compressible starch supplied by Colorcon Ltd, Orpington, Kent.

The ranitidine bismuth citrate and ibuprofen are sieved through a 250μm sieve and blended with the Starch 1500 and magnesium stearate. The resultant mix is filled into size 0 hard gelatin capsules using a suitable filling machine.

|  |  | mg/capsule |
|---|---|---|
| (b) | Ranitidine bismuth citrate | 200.00 |
|  | Indomethacin | 50.00 |
|  | Starch 1500 | 48.50 |
|  | Magnesium stearate | 1.50 |
|  | Fill weight | 300.00 |

The ranitidine bismuth citrate and indomethacin are sieved through a 250μm sieve and blended with the Starch 1500 and magnesium stearate. The resultant mix is filled into size 2 hard gelatin capsules using a suitable filling machine.

EXAMPLE 3

INHIBITION OF INDOMETHACIN-INDUCED GASTRIC LESIONS IN THE RAT

The ability of ranitidine bismuth citrate to prevent indomethacin-induced gastric antral ulceration was compared with that of ranitidine hydrochloride and De-Nol™.

Female rats, which had been fasted for 24 hours and then re-fed, received ranitidine bismuth citrate (1 to 100mg/kg), ranitidine hydrochloride (10 to 100mg/kg) or De-Nol™ (3 to 100mg/kg) by oral gavage. Ranitidine bismuth citrate was administered as a suspension and the other test compounds as solutions. Thirty minutes after dosing with the test compound, animals received indomethacin (60mg/kg sc) as an ulcerogenic stimulus and after a further 6 hours the animals were killed and the antral region assessed macroscopically for damage.

Results are presented in the table below. Ranitidine bismuth citrate produced a dose-related inhibition of indomethacin-induced lesions and was relatively potent, an ED50 value of 4.5mg/kg po being calculated. Ranitidine hydrochloride and De-Nol™ were markedly less potent.

| | $ED_{50}$ Values for Inhibition of Indomethacin - Induced Antral Ulceration | | |
|---|---|---|---|
| Compound | Ranitidine Bismuth Citrate | Ranitidine Hydrochloride | De-Nol ™ |
| $ED_{50}$ mg/kg p.o. | 4.5 | 23.4 | 43.2 |
| 95% confidence limits | 0.5–10.7 | 16.0–33.0 | 23.6–93.0 |

I claim:
1. A method of treating inflammatory conditions or for analgesia in a human or animal subject, which comprises administering to said subject effective amounts of (i) ranitidine bismuth citrate and (ii) a non-steroidal anti-inflammatory drug, wherein the compounds (i) and (ii) are administered as separate compositions, and wherein the method significantly reduces mucosal lesions caused by said non-steroidal anti-inflammatory drug.

2. A method as-claimed in claim 1 in which the non-steroidal anti-inflammatory drug is selected from aspirin, indomethacin, ibuprofen, piroxicam, fenoprofen, ketoprofen, naproxen, mefenamic acid, diflunisal, benorylate, azapropazone, diclofenac, fenbufen, feprazone, fenclofenac, flufenamic acid, flurbiprofen, oxyphenbutazone, phenylbutazone, sulindac and tolmetin.

3. A method as claimed in claim 1 in which compounds (i) and (ii) are in forms suitable for oral administration.

4. A method as claimed in claim 1 in which compound (i) is formulated as a tablet.

5. A method as claimed in claim 4 in which compound (i) is administered at a dosage of 200–800mg per unit dose.

6. The method of claim 1, wherein inflammatory conditions are being treated which conditions are caused by rheumatoid- or osteo-arthritis, or ankylosing spondylitis.

7. The method of claim 1, for analgesia in conditions caused by dysmenorrhoea.

8. A method of treating gastrointestinal damage caused by non-steroidal anti-inflammatory drugs in a human or animal subject, which comprises administering to said subject an effective amount of ranitidine bismuth citrate.

9. A method as claimed in claim 8 in which ranitidine bismuth citrate is formulated as a tablet.

10. A method as claimed in claim 9 in which ranitidine bismuth citrate is administered at a dosage of 200–800mg per unit dose.

11. The method of claim 8 which significantly reduces mucosal lesions caused by said ion-steroidal anti-inflammatory drug in the gastrointestinal tract of a human.

12. A method of treating inflammatory conditions or for analgesia in a human or animal subject, which comprises administering to said subject a pharmaceutical composition comprising an effective amount of ranitidine bismuth citrate and an effective amount of a non-steroidal anti-inflammatory drug, together with a pharmaceutically acceptable carrier or excipient, wherein said method significantly. reduces mucosal lesions caused by said non-steroidal anti-inflammatory drug.

13. A method according to claim 12 wherein the pharmaceutical composition is formulated for oral use.

14. A method according to claim 13 wherein the pharmaceutical composition is in the form of a tablet.

15. A method according to claim 12 wherein the anti-inflammatory drug is aspirin.

\* \* \* \* \*